United States Patent
Brunelle et al.

(10) Patent No.: US 6,677,448 B1
(45) Date of Patent: Jan. 13, 2004

(54) METHOD FOR REACTIVATING A CATALYST FOR CYCLIZING HYDROLYSIS OF AN AMINONITRILE INTO A LACTAM AND USE OF THE REGENERATED CATALYST FOR MAKING LACTAMS

(75) Inventors: Jean-Pierre Brunelle, Croissy-sur-Seine (FR); Christophe Nedez, Salindres (FR)

(73) Assignee: Rhodia Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/744,157

(22) PCT Filed: Jul. 15, 1999

(86) PCT No.: PCT/FR99/01729

§ 371 (c)(1),
(2), (4) Date: Jun. 11, 2001

(87) PCT Pub. No.: WO00/04994

PCT Pub. Date: Feb. 3, 2000

(30) Foreign Application Priority Data

Jul. 22, 1998 (FR) .............................. 98 09528

(51) Int. Cl.$^7$ ................................................ B01J 38/12
(52) U.S. Cl. ..................................................... 540/539
(58) Field of Search ......................................... 540/539

(56) References Cited

U.S. PATENT DOCUMENTS

| 2,357,484 A | 9/1944 | Elmore ........................ 260/239 |
| 4,628,085 A | 12/1986 | Mares et al. ................. 540/539 |
| 5,646,277 A | 7/1997 | Fuchs et al. ................. 540/539 |

FOREIGN PATENT DOCUMENTS

| DE | 21 26 007 | 12/1972 |
| DE | 26 41 429 | 3/1978 |
| EP | 0 388 070 | 9/1990 |
| EP | 0 604 689 | 7/1994 |
| WO | 96 22974 | 8/1996 |

OTHER PUBLICATIONS

Chemical Abstracts, vol. 78, No. 22, Jun. 4, 1973, Columbus, Ohio, US; Abstract No. 140908, Fujita Y. et al, "Reactivation of spent titanium dioxide–copper used in caprolactam synthesis" XP002099193 abstract & JP 47 033081 (TEIJIN LTD.).

Chemical Abstracts, vol. 79, No. 22, Dec. 3, 1973, Columbus, Ohio, Abstract No. 129705, Fujita Y. et al, "Reactivation of Supported copper catalysts" XP002099194 abstract & JP 47 033087 (TEIJIN LTD.).

Chemical Abstracts, vol. 82, No. 26, Jun. 30, 1975, Columbis, Ohio, Abstract No. 175830, Fujita Y. et al, "Activation of catalysts", XP002099195 abstract & JP 49 043474 (TEIJIN LTD.).

*Primary Examiner*—Bruck Kifle
(74) *Attorney, Agent, or Firm*—Burns, Doane, Swecker & Mathis, L.L.P.

(57) ABSTRACT

The present invention relates to a process for regenerating a catalyst for the cyclizing hydrolysis of an aminonitrile for the manufacture of lactams. It relates more particularly to the regeneration of the solid catalysts used in the processes for producing lactams by the cyclizing hydrolysis of aminonitriles. This regeneration process consists in treating the spent catalyst or the catalyst at the end of the cycle at a temperature of between 300° C. and 600° C. with an oxidizing atmosphere.

15 Claims, No Drawings

METHOD FOR REACTIVATING A CATALYST FOR CYCLIZING HYDROLYSIS OF AN AMINONITRILE INTO A LACTAM AND USE OF THE REGENERATED CATALYST FOR MAKING LACTAMS

The present invention relates to a process for regenerating a catalyst for the cyclizing hydrolysis of an aminonitrile for the manufacture of lactams.

It relates more particularly to the regeneration of solid catalysts used in processes for producing lactams by the cyclizing hydrolysis of aminonitriles.

Now, lactams, such as ε-caprolactam, are basic compounds in the manufacture of many products and more particularly in the production of polyamides, such as PA 6 and its copolymers.

Among the various known processes for synthesizing lactams, one of the processes is the cyclizing hydrolysis of the corresponding aminonitrile, more particularly the corresponding unbranched aliphatic aminonitrile, in the presence of water and a catalyst.

The catalysts used in these processes may be classified in several categories—bulk solid catalysts, such as the metal oxides described in Patent Application WO 98/0669, catalysts having a certain porosity, such as the silica described in U.S. Pat. No. 4,628,085, or, more particularly, the activated aluminas described in U.S. Pat. No. 2,357,484 and the porous aluminas described in International Patent Application WO 96/22974, for example.

In processes for the cyclizing hydrolysis of aminonitriles into lactams and more particularly of aminocapronitriles into ε-caprolactam, U.S. Pat. No. 5,646,277 specifies that the reaction is difficult to carry out in the vapour phase, especially on an industrial scale, since the activity of these is unstable.

To avoid these problems, this document recommends carrying out the cyclizing hydrolysis reaction in the liquid phase, possibly in the presence of a solvent.

The abovementioned documents describe the use of heterogeneous catalysis by means of solid catalysts such as aluminas, silicas or metal oxides, for the cyclizing hydrolysis reaction in the vapour phase of an aminonitrile. The cycle time and the instability of these catalysts are not mentioned in these documents since the trials disclosed correspond only to reaction times of a few hours.

The Applicant has noticed in long-term trials, that is to say in trials lasting more than 200 hours, that the abovementioned solid catalysts, and especially certain aluminas, exhibit a somewhat rapid drop in catalytic activity.

One possible solution for improving the economics of the lactam manufacturing process, and more generally the economics of processes using a catalyst, is to regenerate spent catalysts.

However, there are many regeneration processes and, for the same type of catalyst, these regeneration processes often differ depending on the reaction catalysed. Furthermore, depending on the nature of the reaction catalysed, catalyst regeneration may or may not be possible.

This is because the causes of catalyst deactivation are numerous and unpredictable. However, it is also unpredictable that a catalyst treatment for improving some of these properties also regenerates the catalytic activity of the catalyst, at least to an acceptable level.

In the case of a reaction for the cyclizing hydrolysis of an aminonitrile, no document describes the possibility of regenerating the catalysts at the end of the cycle.

One of the objects of the present invention is to remedy these drawbacks by proposing a process for regenerating a catalyst for the cyclizing hydrolysis of an aminonitrile into a lactam.

For this purpose, the invention proposes a process for regenerating a catalyst for the cyclizing hydrolysis of an aminonitrile into a lactam, the said catalyst being a solid, and more generally a simple or mixed oxide which may or may not be porous. This catalyst may also consist of a porous support onto which catalytically active elements are adsorbed or deposited.

This regeneration process consists in treating the spent catalyst or the catalyst at the end of the cycle at a temperature of between 300° C. and 600° C. with an oxidizing atmosphere.

The general characteristic of the reaction for the cyclizing hydrolysis of aminonitriles are described below.

The term "aminonitrile compound" should be understood to mean compounds of the following general formula (I):

$$NM\equiv C\!-\!R\!-\!NH_2 \qquad (I)$$

in which:

R represents a substituted or unsubstituted aliphatic, cycloaliphatic or arylaliphatic radical containing from 3 to 12 carbon atoms.

By way of example, mention may be made of aliphatic aminonitriles, advantageously aliphatic ω-nitriles such as ω-aminovaleronitrile, ω-aminocapronitrile, ω-aminooctanitrile, ω-aminononanitrile, ω-aminodecanitrile, ω-aminodecanonitrile, ω-aminododecanonitrile and methylaminovaleronitrile.

The preferred compound, and the most important, is aminocapronitrile which leads to ε-caprolactam. The latter compound is the monomer for nylon-6 used for the manufacture of various articles, such as moulded parts, yarns, fibres, filaments, cables or films.

Preferably, the invention applies to solid catalysts used especially in cyclizing hydrolysis reactions in the vapour phase.

Thus, a cyclizing hydrolysis reaction requires the presence of water. The molar ratio of the water to the aminonitrile that are involved usually lies between 0.5 and 50 and preferably between 1 and 20. The upper value of this ratio is not critical in the invention, but higher ratios are hardly of any interest for economic reasons.

The cyclizing hydrolysis reaction can be carried out in the liquid or vapour phase.

Thus, in one embodiment, the aminonitrile and water reactants are reacted in the liquid state under pressure, possibly in the presence of a solvent, as described in U.S. Pat. No. 5,646,277, WO 95/14665 and WO 96/00722.

The aminonitrile and the water may be reacted in the form of their mixtures in the vapour state.

In this case, the reactants are maintained in the vapour state in the reactor charged with a defined amount of catalyst.

The free volume of the reactor may be occupied by an inert solid such as, for example, quartz, so as to favour the vaporization and dispersion of the reactants.

It is possible to use, without any inconvenience, as carrier, any inert gas such as nitrogen, helium or argon.

The temperature at which the process of the invention is carried out must be high enough for the reactants to be well and truly in the vapour state. This temperature generally lies between 200° C. and 450° C. and preferably between 250° C. and 400° C.

The time during which the aminonitrile is in contact with the catalyst is not critical. In particular, it may vary depending on the apparatus used. This contact time preferably lies between 0.5 and 200 seconds and even more preferably between 1 and 100 seconds.

The pressure is not a critical parameter of the process. Thus, it is possible to operate at pressures of $10^{-3}$ bar to 200 bar. Preferably, the process is carried out at a pressure of 0.1 to 20 bar.

The process does not exclude the use of a solvent which is inert under the reaction conditions, such as, for example, an alcohol, an alkane, a cycloalkane, an aromatic hydrocarbon or one of these above hydrocarbons in a halogenated form, and thus the presence of a liquid phase in the reaction stream.

These conditions for carrying out the cyclizing hydrolysis reaction are given solely by way of indication.

Specifically, the regeneration process of the invention also applies to the catalysts used in cyclizing hydrolysis reactions used under different conditions, especially to the case of those used when the reaction is carried out a liquid phase possibly in the presence of a solvent, or those used in vapour-phase processes.

The catalysts which may be regenerated by the process of the invention are more particularly mineral oxides having a high porosity, and more advantageously oxides having a macroporosity, that is to say those in which at least part of the pore volume corresponds to pores having a diameter of greater than 500 Å. The pore volume corresponding to the macroporosity is advantageously greater than 5 ml/100 g. These pore-volume and porosity characteristics relate to fresh catalysts and to catalysts regenerated by the process of the invention. This is because one of the important results of the process of the invention is the regeneration of the specific surface area and of the distribution of the pore volume in order substantially to re-establish the characteristics of the fresh catalyst.

As suitable oxides, mention may be made of simple or mixed oxides of the following elements: silicon, titanium zirconium, vanadium, niobium, tantalum, tungsten, molybdenum, iron, rare earths and aluminum.

Thus, the process of the invention applies especially to catalysts based on the aluminas described in Patent Application WO 96/22974 and to such aluminas comprising at least one other simple or mixed oxide of elements, which is adsorbed or supported by the alumina.

Among aluminas suitable for the catalysis of the reaction for the cyclizing hydrolysis of aminonitriles, the regeneration process of the invention applies more particularly and advantageously to aluminas having either a specific surface area greater than 10 m$^2$/g and a total pore volume greater than or equal to 10 ml/100 g, the pore volume corresponding to pores having a diameter greater than 500 Å being greater than or equal to 10 ml/100 g, or a specific surface area greater than 50 m$^2$/g, a total pore volume greater than or equal to 20 ml/100 g and a pore volume corresponding to pores having a diameter greater than 70 Å greater than or equal to 20 ml/100 g, or a specific surface area greater than 50 m$^2$/g, a total pore volume greater than or equal to 15 ml/100 g and a pore volume corresponding to pores having a diameter greater than 200 Å greater than or equal to 15 ml/100 g, preferably greater than or equal to 20 ml/100 g.

Such aluminas are described in Patent Application WO 96/22974.

As mentioned above, these aluminas may also comprise oxides of elements deposited on or adsorbed onto the surface of the pores in order to dope the catalytic activity. The metal oxides may especially be oxides of elements from the following list: silicon, titanium, zirconium, vanadium, niobium, tantalum, tungsten, molybdenum, phosphorus, boron, iron, alkali metals, alkaline-earth metals and rare earths.

The regeneration process of the invention may also apply to catalysts based on simple or mixed metal oxides of the bulk-catalyst type, like those described in Patent Application WO 98/0669.

The process for regenerating the catalysts for the cyclizing hydrolysis of aminonitriles consists, in a preferred characteristic of the invention, in using as oxidizing atmosphere a gas mixture containing at least 0.2% oxygen by volume. Advantageously, this mixture is either an air/inert gas or oxygen/inert gas mixture.

The term "inert gas" should be understood to mean gases which do not have an oxidizing or reducing action, such as nitrogen, rare gases, carbon dioxide and water vapour.

The oxygen content in the treatment gas is advantageously low at the start of the catalyst regeneration process. This oxygen concentration may gradually be increased.

Thus, the oxygen concentration by volume in the treatment gas is preferably between 1% and 10% (limits inclusive) and varies during the process between these two limits.

The catalyst treatment temperature is an important criterion of the process since a treatment at a high temperature results in a catalyst which is regenerated but has a low activity. Thus, the treatment temperature is, according to one preferred characteristic of the invention, between 370° C. and 500° C., and even more advantageously between 370° C. and 450° C.

According to another embodiment of the invention, the oxidizing treatment of the catalysts is advantageously carried out after a pretreatment with water vapour at a temperature of between 200 and 500° C., preferably between 300 and 400° C. The water vapour may be used as a mixture with a carrier gas, such as an inert gas, like nitrogen, or air diluted in an inert gas.

The regeneration process is carried out, for example, in the reactor containing the catalyst by passing through it an oxidizing gas, such as air diluted in an inert gas such as nitrogen. This reactor may be any kind of reactor and may advantageously consist of the catalyst-filled tubes used for the hydrolysis reaction. The process is advantageously carried out at atmospheric pressure.

According to a preferred method of operation, the oxygen concentration is gradually increased, this increase being controlled and slaved to the heat given off by the oxidation of the compounds to be removed. Another way of carrying out the process using a treatment gas containing a higher oxygen concentration consists in removing the heat produced by cooling means in order to prevent the porous catalyst from being sintered.

The invention also relates to a process for manufacturing lactams by the cyclizing hydrolysis of an aminonitrile in the presence of a catalyst. The catalyst is either a mixture of fresh catalyst and of catalyst regenerated according to the process of the invention, or a catalyst regenerated according to the process of the invention.

Further details and advantages of the invention will become more clearly apparent in the light of the examples given below solely by way of indication.

EXAMPLE 1

An alumina having a specific surface area of 139 m$^2$/g has a total pore volume of 117 ml/100 g, with pore volumes, represented by pores having a diameter greater than 70 Å and 500 Å respectively, of 116 ml/100 g and of 50 ml/100 g.

This alumina is used in a reaction for the cyclizing hydrolysis of an aminocapronitrile under operating conditions described below:

Into a cylindrical reactor, 40 mm in diameter and 1 m in height, are loaded 166.5 g of catalyst, this catalyst being distributed in the reactor in the following manner:

66.7 g of catalyst are mixed with 845 g of glass beads in a first reactor portion;

100 g of pure catalyst in a second portion of the reactor.

Water and aminocapronitrile are injected at mass flow rates of 129 g/h and 200 g/h, respectively.

The reactor is maintained at a temperature of 300° C.

The initial degree of conversion of the aminocapronitrile is 99.5%, the initial caprolactam selectivity being greater than 99%.

The trial is stopped after operating for 800 hours.

The degree of conversion of the aminocapronitrile is then 96.5%, the caprolactam selectivity being greater than 99%.

The recovered alumina has a reduced specific surface area (80 m$^2$/g) and a reduced pore volume (88.5 ml/100 g).

This alumina is subjected to a regeneration treatment according to the invention. To do this, the alumina is subjected to a nitrogen gas stream containing 2% oxygen by volume at a flow rate of 1.5 l/min. and a contact time of 20 s. The temperature is increased by 100° C. per hour up to 300° C. and then by 10° C. per hour up to the final treatment temperature. The amount of oxygen contained in the nitrogen is gradually increased from 2 to 7%. The catalyst under the gas stream is maintained for 16 hours at the final temperature of 460° C.

The regenerated alumina has a specific surface area of 134 m$^2$/g and a total pore volume of 109 ml/100 g.

EXAMPLE 2

This regenerated alumina is used in a reaction for the cyclizing hydrolysis of aminocapronitrile under conditions identical to those described in Example 1.

The initial degree of conversion of the aminocapronitrile during the 2nd cycle is 99.4%, the caprolactam selectivity being greater than 99%.

After 500 hours of operation, the degree of conversion of the aminocapronitrile is 96.3%, the caprolactam selectivity still being greater than 99%.

These results, comparable to those obtained using the fresh catalyst during the 1st cycle, demonstrate the effectiveness of the regeneration process of the invention.

What is claimed is:

1. A process for regenerating a catalyst for the cyclizing hydrolysis of an aminonitrile into a lactam, said catalysts comprising a solid oxide, said process consisting essentially of treating said catalyst at a temperature of between 300° C. and 600° C. in an oxidizing atmosphere.

2. The process according to claim 1, wherein the oxidizing atmosphere contains at least 0.2% oxygen by volume.

3. The process according to claim 1, wherein the oxidizing atmosphere is an air/inert gas or oxygen/inert gas mixture.

4. The process according to claim 3, wherein the inert gas is selected from the group consisting of nitrogen, rare gases, carbon dioxide and water vapor.

5. The process according to claim 1, wherein the oxygen concentration in the oxidizing atmosphere is gradually increased during the treatment of the catalyst.

6. The process according to claim 2, wherein the oxygen concentration in the oxidizing atmosphere is between 1% and 10% by volume.

7. The process according to claim 1, wherein the treatment temperature is between 370° C. and 450° C.

8. The process according to claim 1, wherein the catalyst is a simple or mixed oxide of elements in bulk form.

9. The process according to claim 1, wherein the catalyst comprises a simple or mixed mineral oxide of at least one element having at least a pore volume corresponding to pores having a diameter greater than 500 Å.

10. The process according to claim 9, wherein the element or elements are selected from the group consisting of silicon, titanium, zirconium, vanadium, niobium, tantalum, tungsten, molybdenum, iron, rare earths and aluminum.

11. The process according to claim 9, wherein the mineral oxide is alumina.

12. The process according to claim 9, wherein the fresh catalyst has either a specific surface area greater than 10 m$^2$/g and a total pore volume greater than or equal to 10 ml/100 g, the pore volume corresponding to pores having a diameter greater than 500 Å being greater than or equal to 10 ml/100 g, or a specific surface area greater than 50 m$^2$/g, a total pore volume greater than or equal to 20 ml/100 g and a pore volume corresponding to pores having a diameter greater than 70 Å greater than or equal to 20 ml/100 g, or a specific surface area greater than 50 m$^2$/g, a total pore volume greater than or equal to 15 ml/100 g and a pore volume corresponding to pores having a diameter greater than 200 Å greater than or equal to 15 ml/100 g.

13. The process according to claim 9, wherein the porous mineral oxide comprises at least one simple or mixed oxide of elements adsorbed onto or deposited on the surface of the pores, the elements being selected from the group consisting of silicon, titanium, zirconium, vanadium, niobium, tantalum, tungsten, molybdenum, phosphorus, boron, iron, alkali metals, alkaline-earth metals and rare earths.

14. The process according to claim 1, wherein, prior to the treatment with an oxidizing atmosphere, the catalyst to be regenerated is subjected to a treatment with water vapour, optionally as a mixture with a carrier gas comprising inert gases or air diluted with an inert gas, at a temperature of between 200° C. and 500° C.

15. The process for the manufacture of lactams by the cyclizing hydrolysis of an aminonitrile in the presence of a catalyst, wherein the catalyst is a catalyst regenerated according to the process of claim 1, or a mixture of regenerated catalyst and fresh catalyst.

\* \* \* \* \*